(12) United States Patent
Al-Ali (10) Patent No.: US 7,937,128 B2
(45) Date of Patent: May 3, 2011

(54) CYANOTIC INFANT SENSOR

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 827 days.

(21) Appl. No.: 11/171,632

(22) Filed: Jun. 30, 2005

(65) Prior Publication Data

US 2006/0020185 A1    Jan. 26, 2006

Related U.S. Application Data

(60) Provisional application No. 60/586,821, filed on Jul. 9, 2004.

(51) Int. Cl.
*A61B 5/1455* (2006.01)

(52) U.S. Cl. .................................. 600/323; 600/344

(58) Field of Classification Search .................. 600/323, 600/344
See application file for complete search history.

(56) References Cited

U.S. PATENT DOCUMENTS

| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Polczynski |
| 5,163,438 | A | 11/1992 | Gordon et al. |
| 5,337,744 | A | 8/1994 | Branigan |
| 5,431,170 | A | 7/1995 | Mathews |
| 5,437,275 | A | 8/1995 | Amundsen et al. |
| 5,452,717 | A | 9/1995 | Branigan et al. |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |
| 5,584,296 | A | * 12/1996 | Cui et al. ............. 600/479 |
| 5,590,649 | A | 1/1997 | Caro et al. |
| 5,632,272 | A | 5/1997 | Diab et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,685,299 | A | 11/1997 | Diab et al. |
| D393,830 | S | 4/1998 | Tobler et al. |
| 5,743,262 | A | 4/1998 | Lepper, Jr. et al. |
| 5,758,644 | A | 6/1998 | Diab et al. |

(Continued)

FOREIGN PATENT DOCUMENTS

WO    WO 97/03603 A    2/1997

(Continued)

OTHER PUBLICATIONS

PCT International Search Report, App. No. PCT/US 2005/024088, App. Date: Nov. 10, 2005, 6 pages.

*Primary Examiner* — Eric F Winakur (74) *Attorney, Agent, or Firm* — Knobbe, Martens, Olson & Bear LLP (57) ABSTRACT

A pulse oximetry sensor comprises emitters configured to transmit light having a plurality of wavelengths into a fleshy medium. A detector is responsive to the emitted light after absorption by constituents of pulsatile blood flowing within the medium so as to generate intensity signals. A sensor head has a light absorbing surface adapted to be disposed proximate the medium. The emitters and the detector are disposed proximate the sensor head. A detector window is defined by the sensor head and configured so as to limit the field-of-view of the detector.

13 Claims, 7 Drawing Sheets

U.S. PATENT DOCUMENTS

| | | | |
|---|---|---|---|
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,830,136 | A * | 11/1998 | Delonzor et al. ............. 600/323 |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,995,855 | A | 11/1999 | Kiani et al. |
| 5,997,343 | A | 12/1999 | Mills et al. |
| 6,002,952 | A | 12/1999 | Diab et al. |
| 6,011,986 | A | 1/2000 | Diab et al. |
| 6,018,673 | A * | 1/2000 | Chin et al. .................... 600/322 |
| 6,027,452 | A | 2/2000 | Flaherty et al. |
| 6,036,642 | A | 3/2000 | Diab et al. |
| 6,045,509 | A | 4/2000 | Caro et al. |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,236,872 | B1 | 5/2001 | Diab et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,334,065 | B1 | 12/2001 | Al-Ali et al. |
| 6,349,228 | B1 | 2/2002 | Kiani et al. |
| 6,360,114 | B1 | 3/2002 | Diab et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,430,525 | B1 | 8/2002 | Weber et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,515,273 | B2 | 2/2003 | Al-Ali |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kianl et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,697,656 | B1 | 2/2004 | Al-Ali |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,725,075 | B2 | 4/2004 | Al-Ali |
| 6,745,060 | B2 | 6/2004 | Diab et al. |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,792,300 | B1 | 9/2004 | Diab et al. |
| 6,813,511 | B2 | 11/2004 | Diab et al. |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,898,452 | B2 | 5/2005 | Al-Ali et al. |
| 2001/0000790 | A1 * | 5/2001 | Delonzor et al. ............. 600/323 |
| 2002/0173708 | A1 | 11/2002 | DeLonzor et al. |

FOREIGN PATENT DOCUMENTS

| | | |
|---|---|---|
| WO | WO 02/35999 A | 5/2002 |
| WO | WO 02/089664 A | 11/2002 |

* cited by examiner

FIG. 10

CYANOTIC INFANT SENSOR

REFERENCE TO RELATED APPLICATION

The present application claims priority benefit under 35 U.S.C. §119(e) from U.S. Provisional Application No. 60/586,821, filed Jul. 9, 2004, entitled "Cyanotic Infant Sensor," which are incorporated herein by reference.

BACKGROUND OF THE INVENTION

Cyanosis is a congenital condition in which blood pumped to the body contains less than normal amounts of oxygen, resulting in a blue discoloration of the skin. The most common cyanotic condition is tetralogy of Fallot, which is characterized by an abnormal opening, or ventricular septal defect, that allows blood to pass from the right ventricle to the left ventricle without going through the lungs; a narrowing, or stenosis, proximate the pulmonary valve, which partially blocks the flow of blood from the right side of the heart to the lungs; a right ventricle that is abnormally muscular; and an aorta that lies directly over the ventricular septal defect. Another cyanotic condition is tricuspid atresia, characterized by a lack of a tricuspid valve and resulting in a lack of blood flow from the right atrium to the right ventricle. Yet another cyanotic condition is transposition of the great arteries, i.e. the aorta originates from the right ventricle, and the pulmonary artery originates from the left ventricle. Hence, most of the blood returning to the heart from the body is pumped back out without first going to the lungs, and most of the blood returning from the lungs goes back to the lungs.

Figure 1:
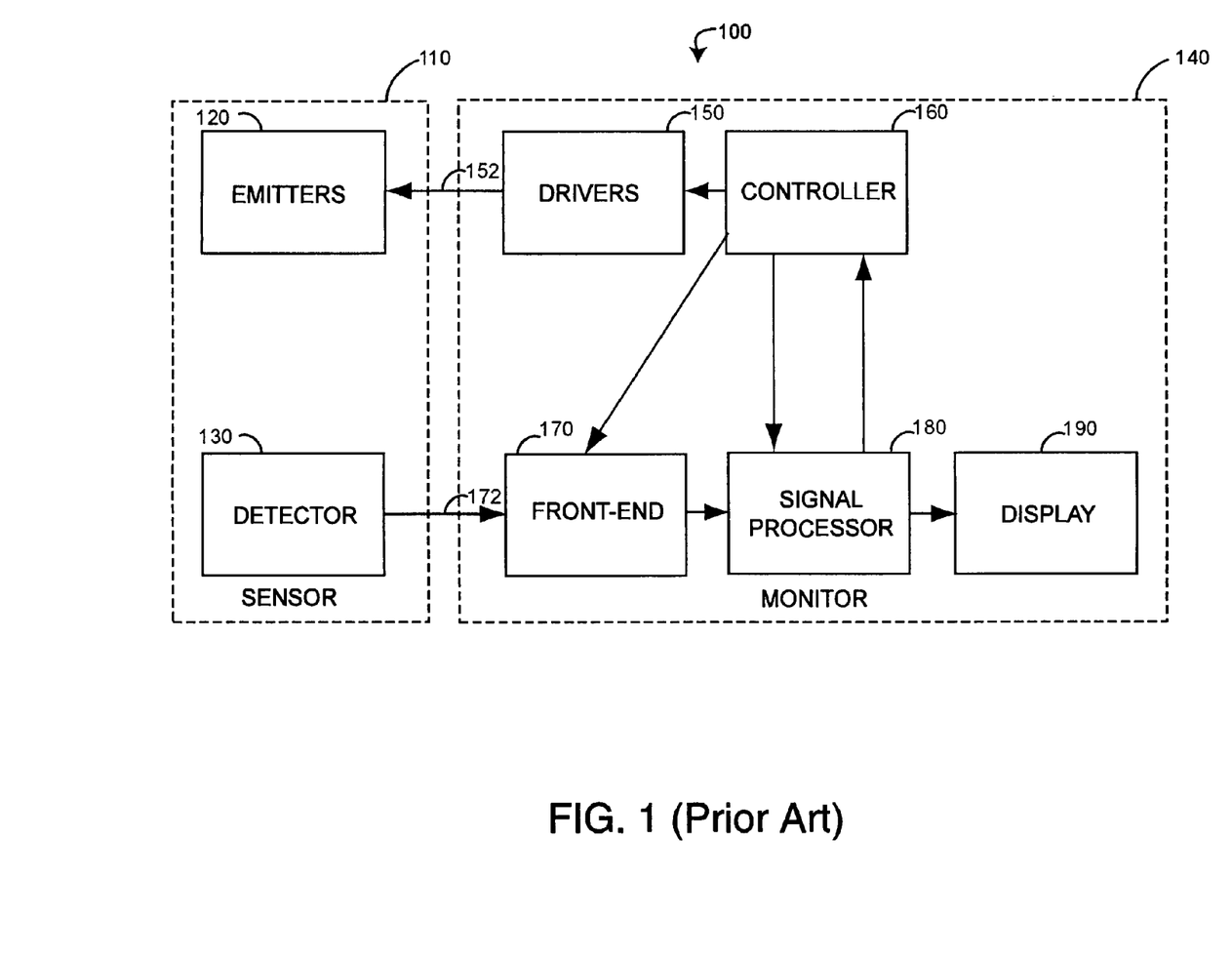
FIG. 1 is a block diagram of a prior art pulse oximetry system.

Pulse oximetry is a useful tool for diagnosing and evaluating cyanotic conditions. A pulse oximeter performs a spectral analysis of the pulsatile component of arterial blood so as to measure oxygen saturation, the relative concentration of oxygenated hemoglobin, along with pulse rate. FIG. 1 illustrates a pulse oximetry system 100 having a sensor 110 and a monitor 140. The sensor 110 has emitters 120 and a detector 130 and is attached to a patient at a selected fleshy tissue site, such as a thumb or toe. The emitters 120 project light through the blood vessels and capillaries of the tissue site. The detector 130 is positioned so as to detect the emitted light as it emerges from the tissue site. A pulse oximetry sensor is described in U.S. Pat. No. 6,088,607 entitled "Low Noise Optical Probe," which is assigned to Masimo Corporation, Irvine, Calif. and incorporated by reference herein.

Also shown in FIG. 1, the monitor 140 has drivers 150, a controller 160, a front-end 170, a signal processor 180, a display 190. The drivers 150 alternately activate the emitters 120 as determined by the controller 160. The front-end 170 conditions and digitizes the resulting current generated by the detector 130, which is proportional to the intensity of the detected light. The signal processor 180 inputs the conditioned detector signal and determines oxygen saturation, as described below, along with pulse rate. The display 190 provides a numerical readout of a patient's oxygen saturation and pulse rate. A pulse oximetry monitor is described in U.S. Pat. No. 5,482,036 entitled "Signal Processing Apparatus and Method," which is assigned to Masimo Corporation, Irvine, Calif. and incorporated by reference herein.

SUMMARY OF THE INVENTION

The Beer-Lambert law provides a simple model that describes a tissue site response to pulse oximetry measurements. The Beer-Lambert law states that the concentration $c_i$ of an absorbent in solution can be determined by the intensity of light transmitted through the solution, knowing the mean pathlength, $mpl_\lambda$, the intensity of the incident light, $I_{0,\lambda}$, and the extinction coefficient, $\epsilon_{i,\lambda}$, at a particular wavelength $\lambda$. In generalized form, the Beer-Lambert law is expressed as:

$$I_\lambda = I_{0,\lambda} e^{-mpl_\lambda \cdot \mu_{a,\lambda}} \tag{1}$$

$$\mu_{a,\lambda} = \sum_{i=1}^{n} \epsilon_{i,\lambda} \cdot c_i \tag{2}$$

where $\mu_{a,\lambda}$ is the bulk absorption coefficient and represents the probability of absorption per unit length. For conventional pulse oximetry, it is assumed that there are only two significant absorbers, oxygenated hemoglobin ($HbO_2$) and reduced hemoglobin (Hb). Thus, two discrete wavelengths are required to solve EQS. 1-2, e.g. red (RD) and infrared (IR).

Figure 2:
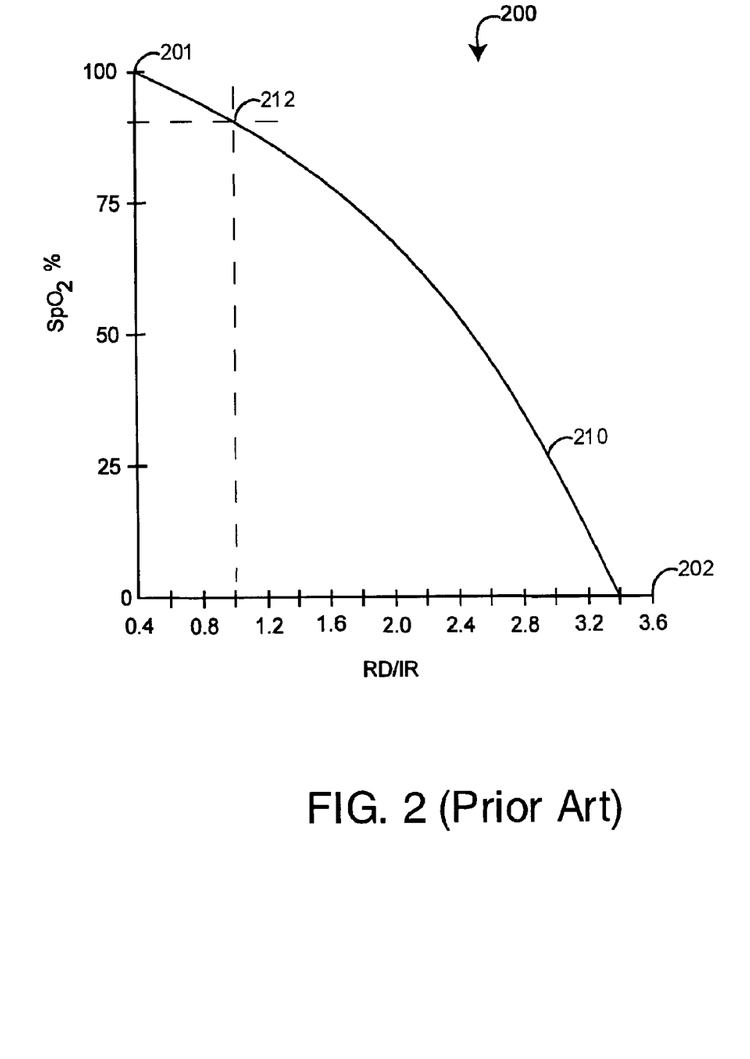
FIG. 2 is an exemplar graph of a conventional calibration curve.

FIG. 2 shows a graph 200 depicting the relationship between RD/IR 202 and oxygen saturation ($SpO_2$) 201, where RD/IR denotes the ratio of the DC normalized, AC detector responses to red and infrared wavelengths, as is well-known in the art and sometimes referred to as the "ratio-of-ratios." This relationship can be approximated from Beer-Lambert's Law, described above. However, it is most accurately determined by statistical regression of experimental measurements obtained from human volunteers and calibrated measurements of oxygen saturation. The result can be depicted as a curve 210, with measured values of RD/IR shown on an x-axis 202 and corresponding saturation values shown on a y-axis 201. In a pulse oximeter device, this empirical relationship can be stored in a read-only memory (ROM) for use as a look-up table so that $SpO_2$ can be directly read-out from an input RD/IR measurement. For example, an RD/IR value of 1.0 corresponding to a point 212 on the calibration curve 210 indicates a resulting $SpO_2$ value of approximately 85%.

Accurate and consistent pulse oximetry measurements on cyanotic infants have been difficult to obtain. An assumption inherent in the calibration curve 210 (FIG. 2) is that the mean pathlength ratio for RD and IR is constant across the patient population. That is:

$$mpl_{RD}/mpl_{IR} = C \tag{3}$$

However, EQ. 3 may not be valid when cyanotic infants are included in that population. The reason may lie in what has been observed as abnormal tissue tone or lack of firmness associated with cyanotic defects, perhaps due to reduced tissue fiber. Such differences in tissue structure may alter the mean pathlength ratio as compared with normal infants. A cyanotic infant sensor addresses these problems by limiting variations in the RD over IR mean pathlength ratio and/or by providing a mean pathlength ratio measure so as to compensate for such variations. Alone or combined, these sensor apparatus and algorithms increase the accuracy and consistency of pulse oximetry measurements for cyanotic infants.

DETAILED DESCRIPTION OF THE PREFERRED EMBODIMENTS

Figure 3A:
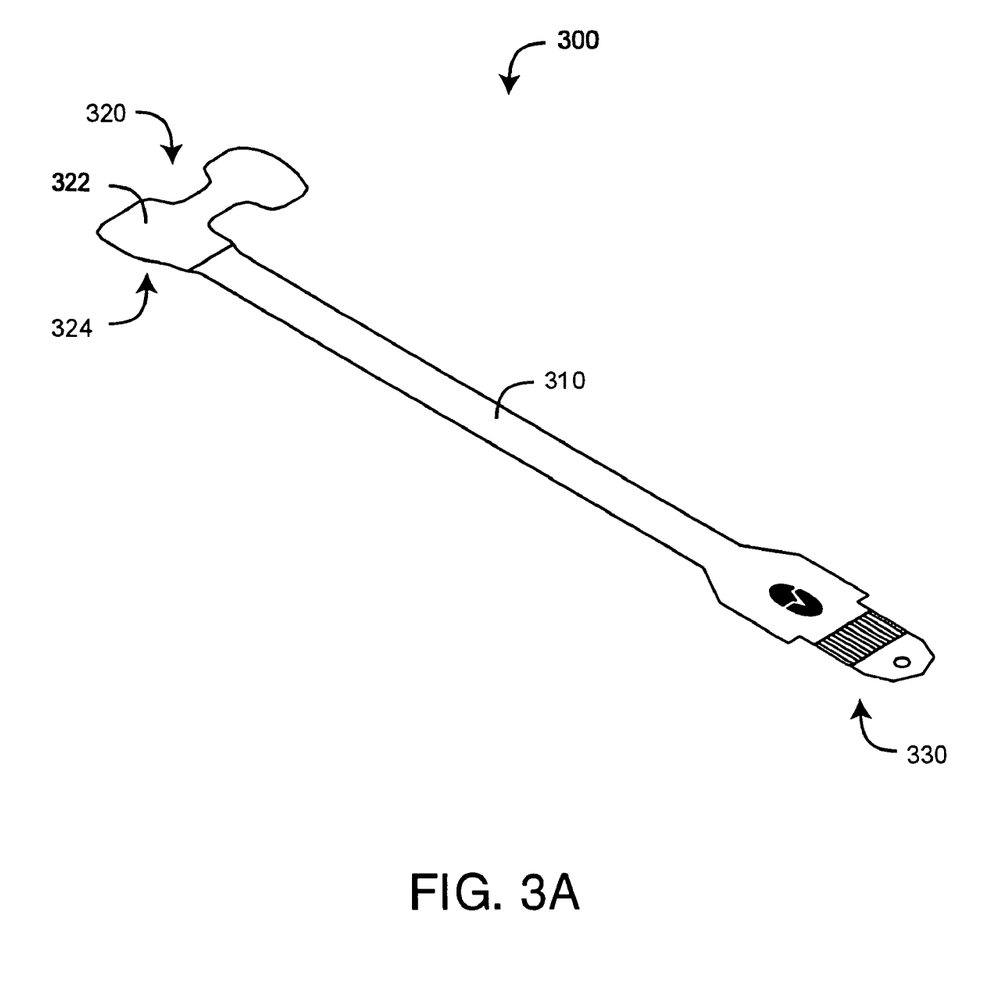
FIGS. 3A-B are a perspective and an exploded perspective views, respectively, of a cyanotic infant sensor embodiment.
Figure 3B:
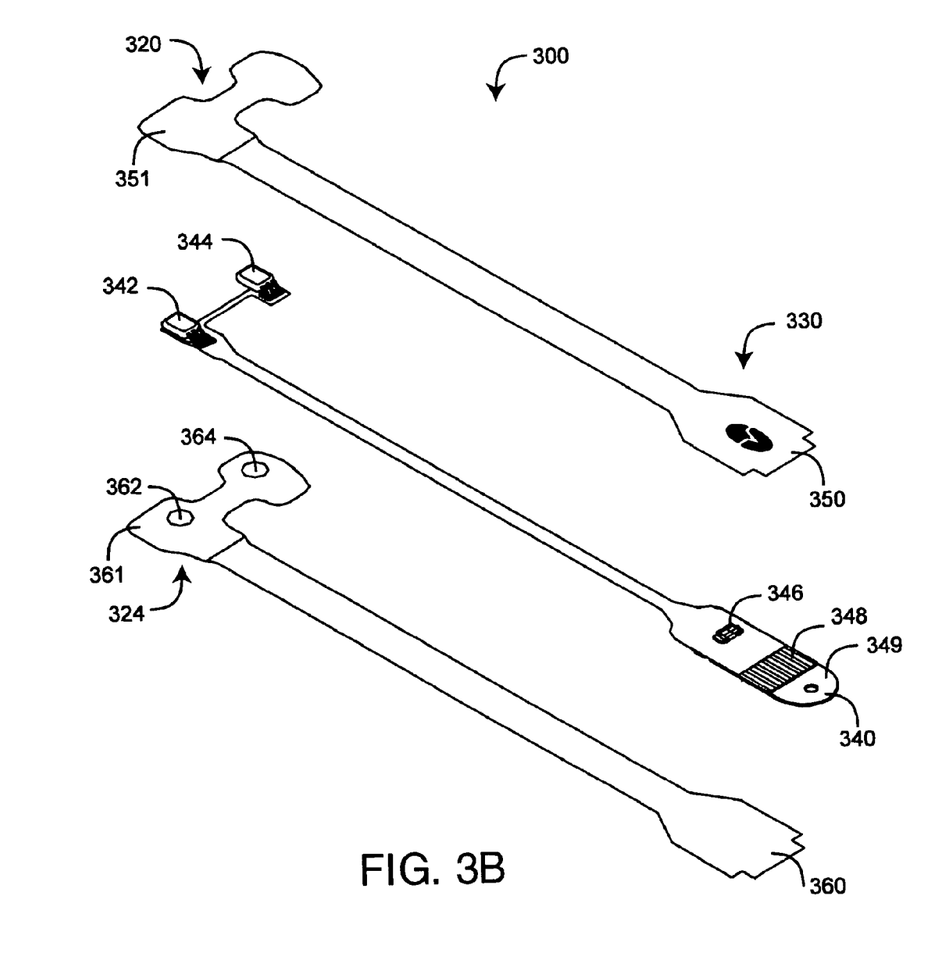

FIGS. 3A-B illustrate one embodiment of a cyanotic infant sensor. The sensor has a light absorbing surface, as described with respect to FIGS. 4-6, below. The sensor also has a detector window configured to limit the detector field-of-view (FOV), as described with respect to FIGS. 7-9, below. Advantageously, these features limit mean pathlength ratio variations that are particularly manifest in cyanotic patients.

The sensor emitters and detector are also matched so as to limit variations in the detector red over IR DC response, i.e. $RD_{DC}/IR_{DC}$, that are not attributed to variations in the mean pathlength ratio (EQ. 3). Such matching advantageously allows for measurement and calibration of the mean pathlength ratio, as described with respect to FIG. 10, below. In one embodiment, cyanotic infant sensors 300 are constructed so that:

$$\lambda_{RD} \approx c_1; \lambda_{IR} \approx c_2 \quad (4)$$

$$I_{0,RD}/I_{0,IR} \approx c_3; \text{ for } i_{DC}(RD), i_{DC}(IR) \quad (5)$$

$$RD_{DC}/IR_{DC} \approx c_4 \quad (6)$$

That is, sensors 300 are constructed from red LEDs and IR LEDs that are each matched as to wavelength (EQ. 4). The LEDs are further matched as to red over IR intensity for given DC drive currents (EQ. 5). In addition, the sensors 300 are constructed from detectors that are matched as to red over IR DC response (EQ. 6). In an embodiment, at least one detector is selected from a plurality of matched detectors each having a first wavelength response over a second wavelength response ratio for at least one predetermined DC incident intensity.

As shown in FIG. 3A, the sensor 300 has a body 310 physically connecting and providing electrical communication between a sensor head 320 and a connector 330. The sensor head 320 houses the emitters and detector and attaches to a patient tissue site. The connector mates with a patient cable so as to electrically communicate with a monitor. In one embodiment, a sensor head surface 324 is constructed of light absorbing material.

As shown in FIG. 3B, the sensor 300 has a face tape 330, a flex circuit 340 and a base tape 360, with the flex circuit 340 disposed between the face tape 330 and the base tape 360. The flex circuit 340 has a detector 342, an emitter 344 with at least two light emitting diodes (LEDs), an information element 346, and contacts 348 disposed on a connector tab 349. Neonatal sensors having a detector, LEDs, an information element, contacts and connector tab are described in U.S. Pat. No. 6,256,523 entitled "Low-Noise Optical Probes," which is assigned to Masimo Corporation, Irvine, Calif. and incorporated by reference herein. In one embodiment, the face tape 350 and base tape 360 are constructed of Betham tape having attached polyethylene head tapes 351, 361. In a particular embodiment, the base head tape 361 is made of black polyethylene, and the face head tape 351 is made of white polyethylene. In one embodiment, a clear tape layer is disposed on the base head tape 361 tissue side over the detector window 362. The base head tape 361 has a detector window 362 and an emitter window 364 each allowing light to pass through the base head tape 361. In one embodiment, the base head tape 361 has a 4 mil thickness and the flex circuit has a 10 mil thickness. The combined 14 mil material thickness functions to limit the detector FOV, as described with respect to FIGS. 6 and 8, below.

Figure 4:
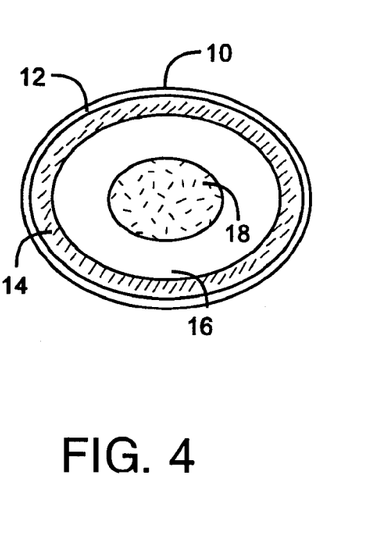
FIGS. 4-5 depict cross-sectional views of a tissue site and an attached pulse oximeter sensor, respectively.
Figure 5:
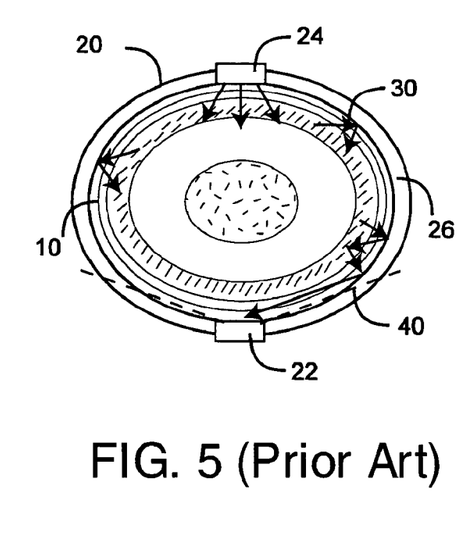
Figure 6:
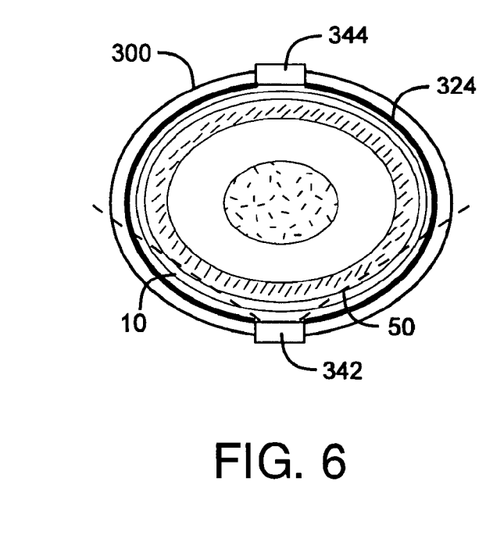
FIG. 6 depicts a cross-sectional view of a tissue site and an attached cyanotic infant sensor.

FIGS. 4-6 illustrate some of the pathlength control aspects of a cyanotic infant sensor 300. FIG. 4 depicts a fleshy tissue site 10 for sensor attachment, such as a finger or thumb 400. The tissue 10 has an epidermis 12, a dermis 14, subcutaneous and other soft tissue 16 and bone 18.

FIG. 5 depicts a conventional pulse oximetry sensor 20 having a detector 22, an emitter 24 and a tape 26 attached to the fleshy tissue 10. Transmitted light 30 propagating from the emitter 24 to the detector 22 that results in a significant contribution to pulse oximetry measurements passes through and is absorbed by the pulsatile blood in the dermis 14. A portion of the transmitted light 30 is scattered out of the epidermis 12 and reflected by the tape 26 back into the fleshy tissue 10. The detector field-of-view (FOV) 40 is relatively wide and, as a result, the detector responds to transmitted light 30 that has propagated, at least in part, outside of the fleshy tissue 10.

FIG. 6 depicts a cyanotic infant sensor 300 that is configured to limit variations in the mean pathlength ratio. In particular, the sensor 300 has a light absorbing tape inner surface 324 that reduces transmitted light reflection back into the tissue site 10, as described with respect to FIGS. 3A-B, above. Further, the detector 342 has a limited FOV 50 so as to reduce the detection of transmitted light that has propagated outside of the tissue site 10, as described in detail with respect to FIGS. 7-9, below.

Figure 7A:
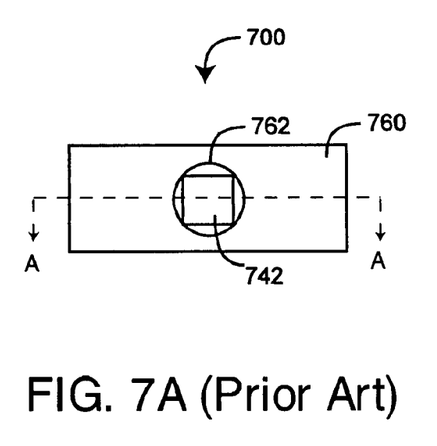
FIGS. 7A-B are plan and cross-sectional sensor head views of a conventional pulse oximeter sensor.
Figure 7B:
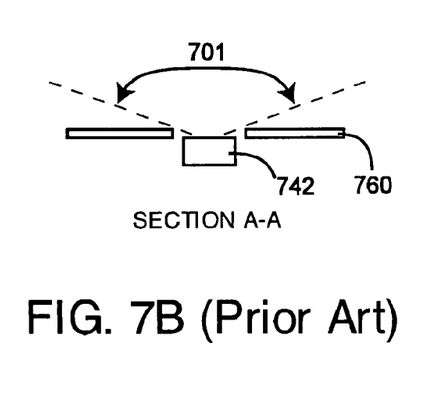
Figure 8A:
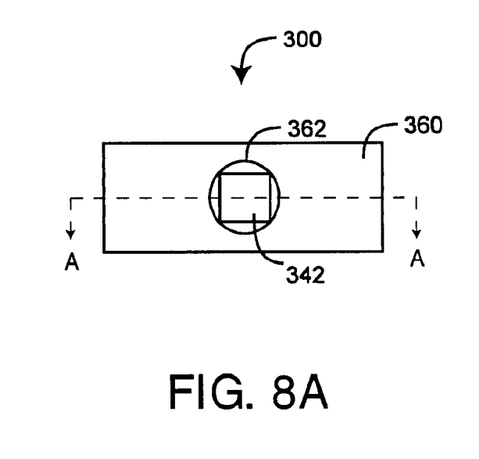
FIGS. 8-9 are plan and cross-sectional sensor head views of cyanotic infant sensor embodiments.
Figure 8B:
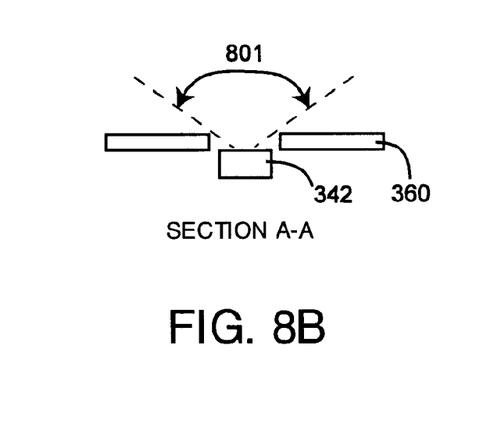
Figure 9A:
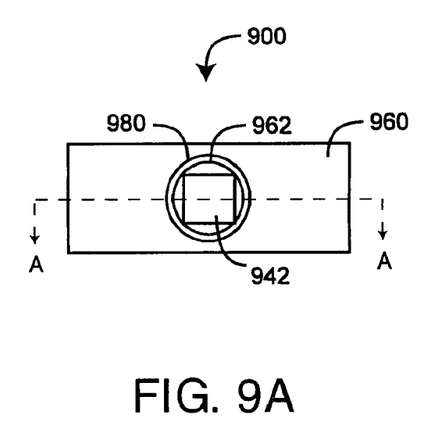
Figure 9B:
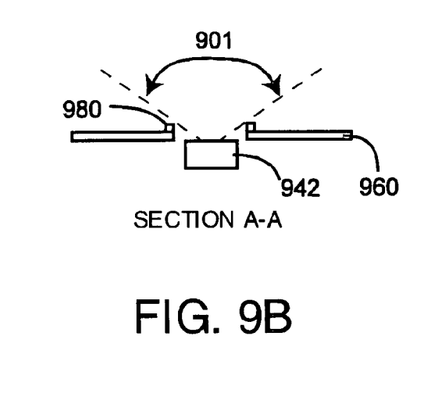

FIGS. 8-9 illustrate cyanotic infant sensor embodiments having a limited detector field-of-view (FOV). FIGS. 7A-B illustrate a conventional sensor 700 having a tape portion 760, a detector window 762 and a detector 742 having a relatively wide FOV 701. In particular, the window thickness does little to restrict the FOV. FIGS. 8A-B illustrate one embodiment of a cyanotic infant sensor 300 having a material portion 360, a detector window 362 and a detector 342 having a restricted FOV 801. In particular, the material thickness 360 functions to define the FOV 801. In one embodiment, the material thickness 360 comprises a flex circuit thickness and a base head tape thickness, as described with respect to FIG. 3B, above. FIGS. 9A-B illustrate another embodiment of a cyanotic infant sensor 900 having a material portion 960, a detector window 962 and a detector 942 having a restricted FOV 901. In particular, an O-ring 980 deposed around the window 962 defines the FOV 901.

Figure 10:
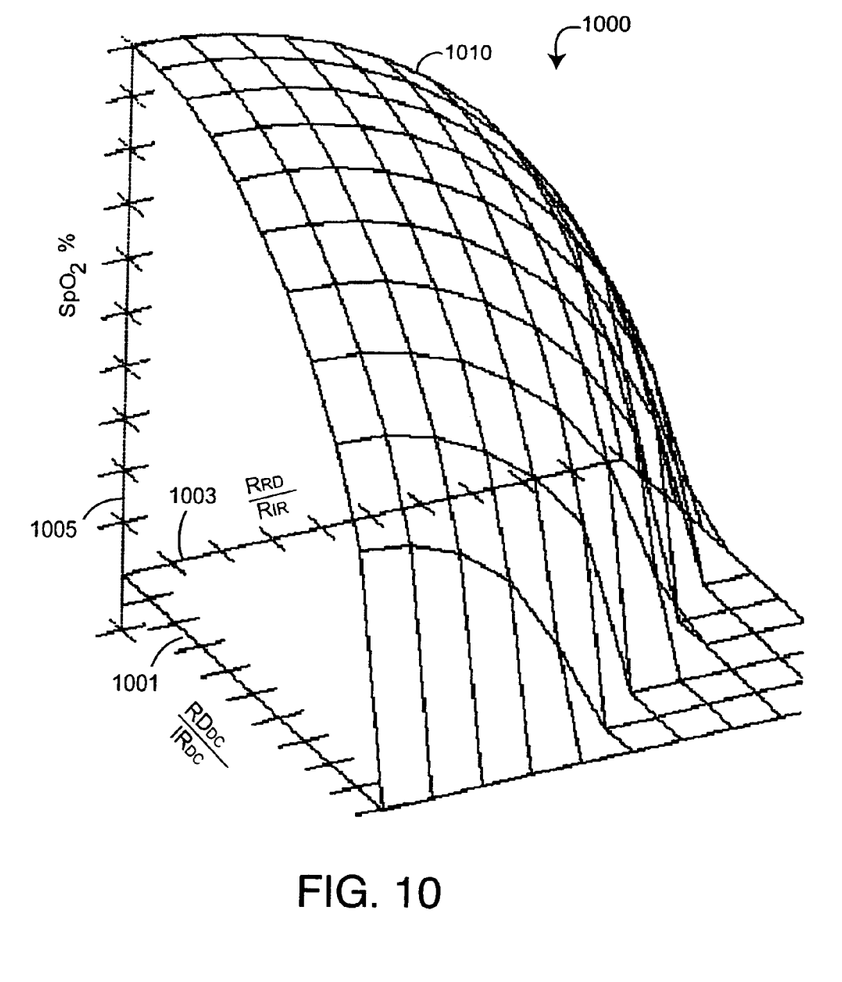
FIG. 10 is an exemplar graph of a calibration surface incorporating a mean pathlength ratio measure.

FIG. 10 depicts an exemplar calibration surface 1000 for a cyanotic infant sensor 300 (FIGS. 3A-B) calculated along a DC response ratio axis 1001, a ratio-of-ratios axis 1003 and a resulting oxygen saturation axis 1005. Matching the emitters and detectors, as described with respect to FIG. 3A, above, allows for pathlength calibration. In particular, variations in the detector DC response ratio ($RD_{dc}/IR_{dc}$) are attributed to variations in the mean pathlength ratio (EQ. 3). As such, a calibration surface is determined by statistical regression of experimental measurements obtained from human volunteers and calibrated measurements of oxygen saturation, as is done for a conventional calibration curve (FIG. 2). A calculated DC response ratio 1001 in combination with a conventionally calculated ratio-of-ratios 1003 is then used to derive an oxygen saturation 1005 for the calibration surface 1000.

A cyanotic infant sensor has been disclosed in detail in connection with various embodiments. These embodiments are disclosed by way of examples only and are not to limit the scope of the claims that follow. One of ordinary skill in art will appreciate many variations and modifications.

What is claimed is:

1. A pulse oximetry sensor comprising:
a plurality of emitters configured to transmit light having a plurality of wavelengths into a fleshy medium, said emitters are selected from a plurality of matched emitters having a first wavelength intensity over a second wavelength intensity ratio for at least one predetermined DC drive current;
at least one detector responsive to said light after absorption by constituents of pulsatile blood flowing within said medium so as to generate a plurality of intensity signals;
a sensor head having a light absorbing surface adapted to be disposed proximate said medium, said head including a face head tape and a base head tape,
said emitters and said at least one detector disposed between said face head tape and said base head tape of said sensor head; and
a detector window defined by said sensor head, said window configured so as to provide a predetermined limit to the field-of-view of said at least one detector during use.

2. The pulse oximetry sensor according to claim 1 wherein said sensor head is configured to attach to a human digit with said light absorbing surface disposed around the periphery of the digit so as to at least partially absorb emitter transmitted light that is scattered out of said digit.

3. The pulse oximetry sensor according to claim 2 wherein a material thickness of said sensor head proximate said detector window limits the field-of-view of said at least one detector.

4. The pulse oximetry sensor according to claim 2 further comprising an O-ring disposed around the periphery of said detector window so as to limit the field-of-view of said at least one detector.

5. A pulse oximetry sensor comprising:
a plurality of emitters configured to transmit light having a plurality of wavelengths into a fleshy medium;
at least one detector responsive to said light after absorption by constituents of pulsatile blood flowing within said medium so as to generate a plurality of intensity signals, said at least one detector selected from a plurality of matched detectors each having a first wavelength response over a second wavelength response ratio for at least one predetermined DC incident intensity;
a sensor head having a light absorbing surface adapted to be disposed proximate said medium, said head including a face head tape and a base head tape,
said emitters and said at least one detector disposed between said face head tape and said base head tape of said sensor head; and
a detector window defined by said sensor head, said window configured so as to provide a predetermined limit to the field-of-view of said at least one detector during use.

6. An oximetry system comprising:
a monitor receiving a sensor signal responsive to light attenuated by body tissue of a monitored patient, the monitor processing said sensor signal to determine measurements for one or physiological parameters of the patient; and
a noninvasive sensor outputting said sensor signal, said sensor including a sensor head including a head tape, a base tape and a flex circuit disposed between said head tape and said base tape, said flex circuit including an emitter and a detector, said emitter comprising a plurality of LEDs, each LED being matched to a red over infrared intensity for a predetermined DC drive current, said base tape including an emitter window and a detector window, each window allowing light to pass through the base tape, said emitter window allowing light to pass through said base tape to said body tissue, said detector window allowing light to pass from said body tissue to said detector, at least one of the emitter window and the detector window limiting a field of view of the corresponding emitter or detector.

7. The oximetry system of claim 6, wherein said base tape layer and said flex circuit combine to limit said field of view.

8. The oximetry system of claim 6, wherein an O-ring disposed around a periphery of said detector window limits said field-of-view.

9. The oximetry system of claim 6, wherein the other of the at least one of the emitter window and the detector window limiting a field of view of the corresponding emitter or detector.

10. The oximetry system of claim 6, wherein said face tape is opaque.

11. The oximetry system of claim 6, wherein said base tape is opaque.

12. The oximetry system of claim 6, wherein the detector is matched to said matched emitters by a red over infrared response for a predetermined DC drive current of said matched emitters.

13. The oximetry system of claim 6, wherein said physiological parameters comprise at least one of oxygen saturation and pulse rate.

* * * * *